United States Patent [19]

Solomon

[11] 4,380,659
[45] Apr. 19, 1983

[54] OLEFIN OXIDATION WITH METHYL FORMATE SOLVENT

[75] Inventor: Paul W. Solomon, Bartlesville, Okla.

[73] Assignee: Phillips Petroleum Company, Bartlesville, Okla.

[21] Appl. No.: 3,064

[22] Filed: Jan. 12, 1979

[51] Int. Cl.³ ............................................ C07D 301/06
[52] U.S. Cl. .................................................. 549/532
[58] Field of Search .................... 260/348.32; 549/532

[56] References Cited

U.S. PATENT DOCUMENTS

| 3,275,662 | 9/1966 | Gash | 260/348.32 |
| 3,281,433 | 10/1966 | Reid | 260/348.32 |
| 3,477,919 | 11/1969 | Lichtenwalter et al. | 260/348.37 |
| 3,818,051 | 6/1974 | Balepin et al. | 260/348.32 |

FOREIGN PATENT DOCUMENTS 917926 2/1963 United Kingdom ........... 260/348.32

OTHER PUBLICATIONS

F. Lanos et al., Chimie et Industrie (Paris) 91, 47-56 (1964) (Transl).
E. G. Hancock, Ed., John Wiley & Sons, N.Y. (1973), Propylene and its Industrial Derivatives, Chapter 7, pp. 273-297.
F. W. Meadus et al., Canadian Jour. Chem. Eng., vol. 42, Apr. 1964, pp. 86-87.

*Primary Examiner*—Norma S. Milestone

[57] ABSTRACT

An olefinically unsaturated compound containing from 3 up to about 18 carbon atoms per molecule and having the formula

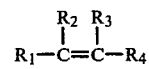

wherein each $R_1$, $R_2$, $R_3$ and $R_4$ is independently selected from a group consisting of hydrogen, alkyl, and cycloalkyl radicals and wherein there is at least one hydrogen attached to a carbon atom adjacent to the olefinic group is oxidized in a liquid reaction medium containing methyl formate. In a preferred embodiment of the invention propylene is oxidized in the presence of methyl formate solvent.

3 Claims, No Drawings

OLEFIN OXIDATION WITH METHYL FORMATE SOLVENT

BACKGROUND OF THE INVENTION

This invention relates to the oxidation of olefins. In one of its aspects this invention relates to the use of a particular solvent in olefin oxidation.

Olefin oxides are extremely useful articles of commerce. They are used as starting materials for the preparation of humectants, lubricants, surfactants, polyethers useful in the preparation of polyurethanes, and the like. An especially useful olefin oxide is propylene oxide. Currently, propylene oxide is prepared from propylene by the classical two-step chlorohydrin route and by oxidation with tertiary-butyl hydroperoxide in the presence of catalysts such as molybdenum salts.

Both of these methods have inherent disadvantages. The chlorohydrin process requires two steps and, because it yields chlorinated by-products, removes expensive chlorine from the process. The tertiary-butyl hydroperoxide method requires the presence of an inorganic catalyst and yields tertiary-butyl alcohol in equimolar quantities to the olefin oxide produced. This tertiary-butyl alcohol must be sold or used.

Numerous reports have been made in the literature regarding methods for the liquid phase oxidation of olefins to olefin oxides with molecular oxygen. Many of these oxidation methods require the presence of catalysts or other additives or secondary treatment of the oxidation mixture with basic materials. Other oxidation methods require the use of certain solvents, such as esters of acetic acid or esters of benzoic acid. None of these liquid phase oxidation methods seems to have been successful enough to result in a commercially acceptable process.

It is therefore an object of this invention to provide a method for the liquid phase oxidation of olefins to olefin oxides with molecular oxygen.

Other aspects, objects, and the various advantages of this invention will become apparent upon reading this specification and the appended claims.

STATEMENT OF THE INVENTION

According to this invention, there is provided a high yield process for the liquid phase oxidation of olefins to olefin oxides that does not require the presence of catalysts or initiators.

According to the present invention, an olefinically unsaturated compound can be oxidized to an olefin oxide with molecular oxygen in high yields in a liquid reaction medium containing methyl formate.

In the currently preferred mode of operation, the methyl formate solvent constitutes greater than about 80 weight percent of the total reaction medium which includes all materials charged to the reactor except molecular oxygen.

In another embodiment of this invention, when the olefin feedstock contains as much as 50 weight percent of saturated compounds, the amount of methyl formate present should be greater than about 60 weight percent of the total reaction mixture and the amount of olefin should be less than about 20 weight percent of the total reaction mixture.

In another embodiment of this invention, the methyl formate solvent is used in combination with diluents or auxiliary solvents which are relatively chemically, oxidatively, and thermally stable under the reaction conditions. In order to retain the benefits of this invention, the amount of methyl formate present should be greater than about 25 weight percent of the total reaction medium and the amount of olefin should be less than about 20 weight percent of the total reaction mixture.

Suitable diluents which can be utilized with the methyl formate solvent of this invention include aromatic hydrocarbons, e.g., benzene, t-butylbenzene, and the like; halogenated benzenes, e.g., chlorobenzene and the like; and aromatic ethers, e.g., diphenyl ether. Although the above diluents have been specifically named, the benefits of the instant invention will be obtained when methyl formate is combined with any diluent that is relatively chemically and oxidatively stable.

Among the olefins suitable for use in this process are those that contain from 3 up to 18 carbon atoms per molecule and can be represented by the following formula I:

wherein each $R_1$, $R_2$, $R_3$, and $R_4$ is independently selected from a group consisting of hydrogen, alkyl, and cycloalkyl radicals and wherein any two of $R_1$, $R_2$, $R_3$, and $R_4$ can be taken together to form an alkylene radical thus forming a cyclic system. An essential limitation on the olefins of general formula I is that there be at least one hydrogen attached to a carbon atom adjacent to the olefinic group, i.e., at least one allylic hydrogen. For reasons of availability and value of the products, the currently preferred olefins for the practice of this invention contain from 3 to 8 carbon atoms per molecule.

Examples of suitable olefins for use in the liquid phase oxidation of this invention include propylene, 1-butene, 2-butene, isobutylene, 2-methyl-1-butene, 4-methyl-2-pentene, 1-hexene, 2-hexene, 3-hexene, 1-octene, 1-decene, 1-dodecene, 1-hexadecene, 1-octadecene, cyclopentene, cyclohexene, cycloheptene, vinyl-cyclohexane, and the like.

Suitable olefin feedstocks for use in this invention include the pure olefin or mixtures of the olefin with as much as about 50 weight percent of saturated compounds. For example, mixtures containing 50 weight percent or more propylene and up to about 50 weight percent propane can be used in quantities up to about 40 weight percent based on the total reaction mixture.

As indicated previously, the reaction of the instant invention is an oxidation reaction wherein an olefinic reactant is converted to an olefin oxide in the presence of methyl formate and, if desired, an additional diluent. The reaction is carried out in the presence of free oxygen. The oxygen can be supplied to the reaction mixture essentially as pure oxygen or admixed with other gases which are essentially inert to the reaction conditions. Air can be utilized as a source of oxygen for the oxidation reaction of this invention. As is generally true for most oxidation reactions, the reaction of this invention can be exothermic and thus some care should be exercised in the amount of oxygen present in the reaction system. The oxygen-containing gas can be introduced into the olefin-solvent mixture incrementally or continuously. Alternately, the reactor can be charged with the olefin and the solvent and then the oxygen-containing gas can be introduced to the desired pressure above the autogenous pressure. The oxygen pressure utilized in this mode of operation will be broadly from about 10 to about 1000 psig (69 to 3447 kPa) and preferably 50 to 350 psig (345 to 2413 kPa) above the autogenous pressure at room temperature.

The reaction temperature used in the olefin oxidation reaction of this invention will generally be from about 100° to about 200° C. The oxidation will proceed too slowly at temperatures below 100° C. and substantial decompositions or explosions can occur at temperatures above about 200° C. The preferred temperature range is from about 125° to about 175° C.

Atmospheric or superatmospheric pressure is suitable for use in this invention. These pressures can range from about 15 psig (103 kPa) to about 3000 psig (20682 kPa). The preferred pressure range is from about 50 psig (345 kPa) to about 1000 psig (6894 kPa). The pressures and temperatures used in the oxidation will depend on the olefin being oxidized and will be selected to maintain a predominantly liquid phase.

The time interval used for the oxidation of this invention will depend on the olefinic compound, temperature, pressure, and the desired degree of completion of the reaction. However, the time interval will generally be within a range of about 1 minute to about 24 hours. A reaction time in the range of about 2 minutes to about 2 hours is currently preferred.

Intimate contact of the reactants, i.e., olefin and molecular oxygen in the solvent, is expected to be of benefit to the oxidation reaction of this invention and conventional means of good mixing by stirring, shaking, and the like can be employed as taught in the prior art. High stirring speed that results in frothing can be detrimental to the oxidation reaction of this invention and should be avoided.

Added catalysts are not required in the oxidation of this invention. As will be shown in the following examples, some compounds that might serve as oxidation catalysts can be present without significantly changing the oxidation results. However, the presence of other compounds that might serve as oxidation catalysts can be detrimental to the oxidation reaction.

While initiators, accelerators, or promoters are not required in the oxidation process of this invention, they can be used to shorten or eliminate the brief induction period. Suitable initiators, accelerators, or promoters include organic peroxides, such as tertiary-butyl hydroperoxide; organic peracids, such as peracetic acid; aldehydes, such as acetaldehyde; and ethers, such as diethyl ether.

Reaction vessels utilized in the process of this invention should be able to withstand the pressures and oxidizing conditions which are present. The reaction vessel can be made of various materials including stainless steel, Monel, and titanium and can also be glass-lined.

A variety of methods can be utilized for the recovery of the reaction products, unreacted olefinic starting material, and solvent. Following removal of the liquid and gaseous materials from the reactor, various combinations of conventional techniques for separation of the desired product, unreacted olefin, and solvent including distillation, fractionation, extractions, and the like can be employed. When propylene oxide is the reaction product, the propylene oxide-methyl formate mixture can be separated by extractive distillation using saturated aliphatic hydrocarbons, such as n-hexane, n-heptane, n-decane, n-dodecane, and the like, and mixtures thereof as the solvent. The methyl formate is removed overhead and the propylene oxide and solvent are removed in the bottoms stream.

EXAMPLES

The reactor utilized in the following examples was a 300 ml 316 stainless steel autoclave equipped with a variable speed stirrer and indicators for temperature and pressure. The propylene used was Polymerization Grade (Phillips Petroleum Company). All solvents were commercially available and were distilled before use. The results of the runs are expressed in terms of the percent propylene converted during the reaction time and the mole percent selectivity to propylene oxide based on the amount of propylene converted.

EXAMPLE I

A series of runs was carried out in which propylene was oxidized in several solvents to demonstrate the advantage of the instant invention. In each run the autoclave was charged with 87 g of the solvent. The autoclave was sealed and 12 g (286 mmoles) of propylene was added to the autoclave as a gas at room temperature through a gas inlet tube. Oxygen was added to the autoclave through the gas inlet tube to an oxygen pressure of 200 psig (1379 kPa) above the autoclave pressure at room temperature. The autoclave was heated to 150° C. and maintained at that temperature with stirring at 250 rpm for a reaction period of 135 minutes. At the conclusion of the reaction period, the autoclave was cooled and vented through a dry ice trap and tared tubes containing, first, Ascarite for $CO_2$ removal, and later 5 A Molecular Sieve. The dry ice trap was warmed to room temperature and the gases were passed through a dry test meter to determine the amount of propylene present. The liquid in the dry ice trap was combined with the liquid in the autoclave and analyzed by gas liquid chromatography (glc). The amount of unreacted propylene was determined by totaling the quantities in the molecular sieves, dry ice trap bleed-off, and in the liquid product. The results obtained in these runs are presented in Table I.

TABLE I

| Run No. | Solvent | Propylene Conversion, % | Selectivity to Propylene Oxide, % |
|---|---|---|---|
| 1 | Methyl Formate | 21 | 51 |
| 2 | Methyl Formate | 25 | 55 |
| 3 | Methyl Formate | 25 | 49 |
| 4 | Ethyl Formate | 29 | 33 |
| 5 | n-Butyl Formate | 33 | 26 |
| 6 | Methyl Acetate | 32 | 30 |
| 7 | Ethyl Acetate | 26 | 37 |
| 8 | Propylene Glycol Diacetate | 34 | 28 |
| 9 | Dimethyl Carbonate | 27 | 32 |
| 10 | Benzene | 27 | 21 |
| 11 | Methylene Chloride | 24 | 10 |
| 12 | Propionitrile | 29 | 24 |
| 13 | N,N—Dimethylformamide | 12 | 8 |

The results presented in Table I show that the use of methyl formate as a solvent for the oxidation of propylene to propylene oxide results in a significantly higher selectivity to propylene oxide than runs in a wide variety of other solvents. The significant differences in selectivities between invention runs 1 to 3 and runs 4 to 9 using other esters is surprising in view of the structural similarities between methyl formate and other esters such as ethyl formate and methyl acetate.

EXAMPLE II

A series of runs was carried out to demonstrate the criticality of the amount of methyl formate present during the oxidation of propylene. Each run was conducted using the procedure of Example I (with 87 g of methyl formate in each run) except that the amount of propylene was different in each run and a reaction time of 250 minutes was required in run 14 to reach an 18 percent propylene conversion. The results of these runs are presented in Table II.

TABLE II

| Run No. | Methyl Formate in Reaction Mixture[a], Weight % | Propylene Conversion, % | Selectivity to Propylene Oxide, % |
|---|---|---|---|
| 14[b] | 94 | 18 | 49 |
| 2 | 88 | 25 | 55 |
| 15 | 81 | 18 | 39 |
| 16 | 74 | 19 | 25 |

[a]Weight percent methyl formate based on the total reaction mixture weight.
[b]Reaction time = 250 minutes.

The results of runs in Table II show that at levels of methyl formate below about 80 weight percent (based on the weight of the total reaction mixture) selectivity to propylene oxide decreases significantly.

EXAMPLE III

A series of runs was carried out to demonstrate the process of this invention for the oxidation of propylene to propylene oxide using mixtures of methyl formate and benzene. The procedure of Example I was followed in each run except that various ratios of methyl formate to benzene (all to a total of 87 g) were used. The quantities of methyl formate and benzene used in each run and the results are shown in Table III.

TABLE III

| Run No. | Methyl Formate, g | Benzene g | Methyl[a] Formate, Weight % | Propylene Conversion, % | Selectivity to Propylene Oxide, % |
|---|---|---|---|---|---|
| 10 | — | 87 | 0 | 27 | 21 |
| 17 | 5.4 | 82 | 5 | 25 | 33 |
| 18 | 27 | 60 | 27 | 27 | 43 |
| 3 | 87 | — | 88 | 25 | 49 |

[a]Weight percent methyl formate based on the combined weight of methyl formate, benzene, and propylene.

The results shown in Table III demonstrate the process of this invention for the oxidation of propylene to propylene oxide in mixtures of methyl formate and benzene and show that the amount of methyl formate in the mixture is a critical factor in obtaining high selectivities to propylene oxide. Although methyl formate levels as low as 5 weight percent (run 17) result in an improvement in percent selectivity to propylene oxide over a run using only benzene (run 10), the significantly higher selectivities of the instant invention are realized at methyl formate levels above about 25 weight percent.

EXAMPLE IV

Another series of runs was conducted to show the effect of reaction time and initial oxygen pressure on the selectivities of the oxidation of propylene to propylene oxide in methyl formate. The procedure described in Example I was followed in each run except that the reaction times and initial oxygen pressures above the autogenous reactor pressure at room temperature were varied. The results of these runs are shown in Table IV.

TABLE IV

| Run No. | Reaction Time, min. | Initial Oxygen Pressure[a], psi (kPa) | Propylene Conversion, % | Selectivity to Propylene Oxide, % |
|---|---|---|---|---|
| 19 | 70 | 204(1406) | 14 | 47 |
| 1 | 135 | 209(1441) | 21 | 51 |
| 20 | 80 | 408(2813) | 29 | 31 |
| 21 | 135 | 440(3033) | 46 | 37 |

[a]Oxygen pressure above the autogenous reactor pressure at room temperature.

The results shown in Table IV show that at both levels of initial oxygen pressure the selectivities to propylene oxide are better at the longer reaction times. The higher selectivities to propylene oxide in runs 19 and 1 to about 200 psi compared with runs 20 and 21 at about 400 psi indicate that the lower initial oxygen pressure is beneficial.

EXAMPLE V

Several runs were conducted to show the effect of stirrer speed on the oxidation of propylene to propylene oxide in methyl formate. The procedure described in Example I was followed in each run except that the stirring speeds and initial oxygen pressures used in each run and the results obtained are presented in Table V.

TABLE V

| Run No. | Initial Oxygen Pressure, psi (kPa) | Stirrer Speed, rpm | Propylene Conversion, % | Selectivity to Propylene Oxide, % |
|---|---|---|---|---|
| 1 | 209(1441) | 250 | 21 | 51 |
| 22 | 202(1392) | 1000 | 27 | 44 |
| 21 | 440(3033) | 250 | 46 | 37 |
| 23 | 420(2895) | 1000 | 48 | 24 |

The results described in Table V indicate that at both initial oxygen pressures, the higher stirrer speed resulted in lower selectivities to propylene oxide. It is currently believed that the higher stirrer speed resulted in a frothing action that is detrimental to propylene oxide formation.

EXAMPLE VI

A series of runs was carried out to determine the effect of various added materials on the oxidation of propylene to propylene oxide in methyl formate. The procedure described in Example I was followed except that the added materials were charged to the autoclave with the methyl formate solvent. The materials added and the results observed in each run are presented in Table VI along with run 1, which is included for comparison.

TABLE VI

| Run No. | Added Component, (mmole) | Propylene Conversion, % | Selectivity to Propylene Oxide, % |
|---|---|---|---|
| 1 | none | 21 | 51 |
| 24 | Acetaldehyde (10) | 27 | 52 |
| 25 | Acrolein (30) | 30 | 48 |
| 26 | Boric Acid (16) | 28 | 47 |
| 27 | NaHCO$_3$ (40) | 21 | 53 |
| 28 | t-Butyl Hydroperoxide (10) | 34 | 41 |

The presence of acetaldehyde (run 24), acrolein (run 25), and t-butyl hydroperoxide (run 28) during the oxidation resulted in a reduction of the induction time, but made no significant improvement in the selectivity to propylene oxide. The presence of boric acid (run 26) had virtually no effect on the oxidation of propylene. Sodium bicarbonate had little influence on the oxidation reaction.

EXAMPLE VII

A series of runs was carried out to determine the effect of various compounds that, based on prior oxidation knowledge, would be expected to act as oxidation catalysts on the oxidation of propylene to propylene oxide in methyl formate. The procedure described in Example I was followed in each run except that the potential catalyst was charged to the reactor with the methyl formate solvent. The following materials had no significant effect on the selectivity to propylene oxide.

| Run No. | Added Material (g) | |
|---|---|---|
| 29 | $ZrO_2$ | (1) |
| 30 | CuO | (1) |
| 31 | Co(acac)$_2$* | (0.1) |
| 32 | NiO | (1) |
| 33 | $MnO_2$ | (1) |

*acac = acetylacetonate

The following materials were detrimental at the indicated levels to the production of propylene oxide.

| Run No. | Added Material (g) | |
|---|---|---|
| 34 | $MoO_2$ | (1) |
| 35 | $V_2O_5$ | (1) |
| 36 | $Cu_2O$ | (1) |
| 37 | Cu(acac)$_2$* | (0.1) |
| 38 | $SiO_2$ | (1) |
| 39 | $WO_3$ | (1) |
| 40 | $V_2O_3$ | (1) |

*acac = acetylacetonate

EXAMPLE VIII

Several extractive distillation runs were carried out to demonstrate the separation of methyl formate-propylene oxide mixtures using n-heptane as the solvent. A 9/1 weight ratio mixture of methyl formate/propylene oxide was distilled through a 1" (2.5 cm)×18" (43 cm) long column packed with glass helices while n-heptane was metered into the top of the column at various rates. The results obtained in these runs are shown below.

| n-Heptane/Distillate Volume ratio | Methyl Formate in Overhead[a], Weight % |
|---|---|
| 0 | 90 |
| 2 | 96 |
| 4 | 98 |
| 6 | 99 |

[a]Weight percent methyl formate based on the combined methyl formate-propylene oxide weight.

As the n-heptane/distillate volume ratio increases, the amount of methyl formate in the overhead increases and the propylene oxide is concentrated in the bottoms fraction.

The attempted oxidation of ethylene, an olefin outside the scope of the olefins of this invention, in methyl formate was not successful. The oxidation of neohexene, an olefin outside the scope of this invention, in methyl formate gave about the same results as a run using t-butylbenzene as solvent.

I claim:

1. A method for oxidizing an olefin containing from 3 up to about 18 carbon atoms per molecule which is represented by the formula

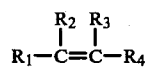

wherein each $R_1$, $R_2$, $R_3$, and $R_4$ is independently selected from a group consisting of hydrogen, alkyl, and cycloalkyl radicals and wherein there is at least one hydrogen attached to a carbon atom adjacent to the olefinic group said method comprising contacting said olefin with molecular oxygen in a liquid reaction medium consisting essentially of said olefin and methyl formate said methyl formate present in the reaction medium in a minimum amount of about 80 weight percent.

2. A method of claim 1 wherein the reaction temperature is in the range of about 100° C. to about 200° C.

3. A method of claim 1 wherein the reaction temperature is in the range of about 125° C. to about 175° C.

* * * * *